US00PP16998P3

(12) United States Plant Patent
Suzuki et al.

(10) Patent No.: US PP16,998 P3
(45) Date of Patent: Aug. 15, 2006

(54) ***VERBENA* PLANT NAMED 'SUNMARISAKURA'**

(50) Latin Name: *Verbena hybrida*
Varietal Denomination: Sunmarisakura

(75) Inventors: Kenichi Suzuki, Ibaraki (JP); Yasunori Yomo, Kawasaki (JP); Naoto Takamura, Omihachiman (JP)

(73) Assignee: Suntory Flowers Limited, Tokyo (JP)

( * ) Notice: Subject to any disclaimer, the term of this patent is extended or adjusted under 35 U.S.C. 154(b) by 1 day.

(21) Appl. No.: 10/789,430

(22) Filed: Feb. 27, 2004

(65) Prior Publication Data

US 2005/0138713 P1 Jun. 23, 2005

(30) Foreign Application Priority Data

Dec. 19, 2003 (JP) ..... 16477

(51) Int. Cl.
*A01H 5/00* (2006.01)

(52) U.S. Cl. ..... Plt./308
(58) Field of Classification Search ..... Plt./308
See application file for complete search history.

(56) References Cited

U.S. PATENT DOCUMENTS

PP11,130 P * 11/1999 Yomo et al. ..... Plt./308

FOREIGN PATENT DOCUMENTS

JP PBR 4900 2/1996

JP PBR 8144 6/2000

OTHER PUBLICATIONS

Fehr, Principles of Cultivar Development, pp 287–303, 1987.* http://www.hort.net/gallery/view/ver/vertecb/, Mar. 12, 2005.*

Suntory Flowers Ltd., "Flower & Green, the newest catalog 2004" Published Oct. 10, 2003.

Suntory Flowers Ltd., "Flower & Green, the newest catalog 2002" Published 2001.

Jackson & Perkins wholesale, Inc., USA, "The 2004 Suntory Collection" Published 2003.

Moerheim New Plant bv., USA, "The Suntory Collection 2004" Published 2003.

Botanicals Pty Ltd., AU., "The Color Wave Collection 2003–4" Published 2002.

* cited by examiner

*Primary Examiner*—Anne Marie Grunberg
*Assistant Examiner*—Georgia Helmer
(74) *Attorney, Agent, or Firm*—Christie, Parker & Hale, LLP.

(57) ABSTRACT

Disclosed herein is a *Verbena* plant having a decumbent growth habit and long stems. The plant forms flowers in clusters with a great profusion of blooms. The flowering duration is long and the entire plant remains in bloom for a considerable period of time. The flower size is large and the petal color of flowers is light purplish pink. The plant is highly tolerant to heat, pests and diseases, particularly powdery mildew, and is moderately resistant to cold. 'Sunmarisakura' does not freely set seed due to self-sterility.

2 Drawing Sheets

Botanical classification: *Verbena hybrida.*
Varietal denomination: 'Sunmarisakura'.

BACKGROUND OF THE VARIETY

The present new distinct cultivar of *Verbena* was created by heavy ion beam irradiation of the *Verbena* hybrid variety called 'Sunmarisa'. 'Sunmarisa' (U.S. Plant Pat. No. 11,130) is our *Verbena* hybrid variety grown at Yokaichi-shi, Shiga-ken, Japan.

In July 1998, 5Gy of ionic nitrogen (135 MeV) was irradiated onto 128 pieces of in vitro axillary bud of 'Sunmarisa' using the Ring Cyclotron at The Institute of Physical and Chemical Research. Two weeks later, elongated buds were grown from cuttings. In March 1999, five varieties were selected in view of self-sterility. These plants were propagated by cutting and then grown in pot and planter box on trial from May 1999 at Yokaichi-shi, Shiga-ken, Japan. Additionally, the plants were grown in pots and planter boxes during trial in 2000. Finally, one plant was selected from these five varieties in view of having a long flower duration. By November 2000, the botanical characteristics of the selected plant were examined. As a result, it was concluded that this new *Verbena* plant is distinguishable from any other variety, whose existence is known to us, and is uniform and stable in its characteristics. This new variety of *Verbena* plant was named 'Sunmarisakura'.

The new variety of the present invention can be distinguished from its parent 'Sunmarisa' in its self-sterility. Also the new variety can be distinguished from the similar variety 'Sunmaripi' in the flower color and self-sterility.

The new variety of *Verbena* plant 'Sunmarisakura' was asexually reproduced by cutting at Yokaichi-shi, Shiga-ken, Japan, and the homogeneity and stability thereof were confirmed. The instant plant retains its distinctive characteristics and reproduces true to type in successive generations.

In the following description, the color-coding is in accordance with The Horticultural Colour Chart of The Royal Horticultural Society, London, England (R.H.S.).

'Sunmarisa' was used to produce the new variety, 'Sunmarisakura'. The botanical characteristics of 'Sunmarisa' are as follows when grown at Yokaichi-shi, Shiga-ken, Japan.

Plant:
*Growth habit*.—Decumbent.
*Plant width*.—Approximately 65–71 cm.
*Plant height*.—Approximately 8–9 cm.
Stem:
*Diameter*.—Approximately 1.7–2.2 mm.
*Anthocyanin pigmentation*.—Absent.
*Pubescence*.—Normal.
*Branching*.—A moderate level of branching is present.
*Subterranean stem*.—Absent but when the stems contact the surface of soil, the nodes take root in the ground and the plant growth thereby spreads.
*Length of internodes*.—Approximately 1.7–2.7 cm.
Leaf:
*Phyllotaxis*.—Opposite.
*Shape*.—Oblong-lanceolate.
*Depth of incision*.—Shallow.
*Margin*.—Serrate.
*Length*.—Approximately 2.9–3.6 cm.
*Width*.—Approximately 1.6–2.4 cm.
*Leaf apex*.—Mucronate.
*Leaf base*.—Petiolate.
*Color*.—Dark olive green (near R.H.S. 141A) on the upper surface.
*Pubescence*.—Sparse.
*Petiole*.—Present.
*Thickness of petiole*.—Approximately 1.0–1.2 mm.
*Length of petiole*.—Approximately 1.2–2.5 mm.
Flower:
*Shape of cluster*.—Obovate.
*Length of cluster*.—Approximately 2.3–4.4 cm.
*Diameter of cluster*.—Approximately 4.0–5.8 cm.
*Facing direction*.—Upward.
*Outward curvature of petal*.—Flat.
*Diameter*.—Approximately 1.8–1.9 cm.
*Height*.—Approximately 2.1–2.2 cm.
*Color*.—Light purplish pink (near R.H.S. 62C) on the upper surface.
*Eye color*.—Pale yellow (near R.H.S. 11D).
*Variegation on petal*.—Absent.
*Color presentation*.—Substantially even.
*Color intensity*.—Absent.
*Overlapping of petals*.—Separate.
*Incision of petal*.—Present.
*Number of petals*.—5.
*Sepal*.—Tubular in configuration.
*Length of calyx*.—Approximately 1.2–1.4 cm.
*Anthocyanin pigmentation of calyx limb*.—Absent.
*Shape of pistil*.—Two lobes.
*Color of anther*.—Yellowish green.
*Diameter of peduncle*.—Medium.
*Length of peduncle*.—Medium.
*Number of flowers*.—Many.
*Flower bearing*.—In a cluster.
*Reproductive organs*.—1 pistil and 4 stamens.
*Pollen*.—Brilliant greenish-yellow (near R.H.S. 6C) in coloration.
*Flower fragrance*.—Absent.
*Flowering time*.—Early.
*Flowering duration*.—Long. When planted during March, the plant commonly blooms from April to November. A bloom cluster commonly is present for approximately 2 to 3 weeks, and an individual bloom within the cluster commonly lasts for approximately 7 to 10 days on the plant. The plant is highly tolerant to heat, and exhibits a high resistance to diseases, particularly powdery mildew, and a high resistance to pests.

'Sunmaripi' was used as a comparison for this new variety 'Sunmarisakura'. The botanical characteristics of the 'Sunmaripi' are as follows when grown at when grown at Yokaichi-shi, Shiga-ken, Japan.

Plant:
*Growth habit*.—Decumbent.
*Plant width*.—Approximately 60 cm.
*Plant height*.—Approximately 20 cm.
Stem:
*Diameter*.—Approximately 2.5 mm.
*Anthocyanin pigmentation*.—Present.
*Pubescence*.—Normal.
*Branching*.—A moderate level of branching is present.
*Subterranean stem*.—Absent but when the stems contact the surface of soil, the nodes take root in the ground and the plant growth thereby spreads.
*Length of internode*.—Approximately 4.5 cm.
Leaf:
*Phyllotaxis*.—Opposite.
*Shape*.—Oblong-lanceolate.
*Depth of incision*.—Shallow.
*Margin*.—Serrate.
*Length*.—Approximately 3.5 cm.
*Width*.—Approximately 2.2 cm.
*Leaf apex*.—Mucronate.
*Leaf base*.—Petiolate.
*Color*.—Grayish olive green (near R.H.S. 147A) on the upper surface.
*Pubescence*.—Sparse.
*Petiole*.—Present.
*Thickness of petiole*.—Approximately 1.0 mm.
*Length of petiole*.—Approximately 2.0 mm.
Flower:
*Shape of cluster*.—Obovate.
*Length of cluster*.—Approximately 3.2 cm.
*Diameter of cluster*.—Approximately 5.2 cm.
*Facing direction*.—Upward.
*Outward curvature of petal*.—Flat.
*Diameter*.—Approximately 1.7 cm.
*Height*.—Approximately 2.0 cm.
*Color*.—Deep purplish pink (near R.H.S. 77B) on the upper surface.
*Eye color*.—Pale yellow (near R.H.S. 11D).
*Variegation on petal*.—Absent.
*Color presentation*.—Substantially even.
*Color intensity*.—Absent.
*Incision of petal*.—Present.
*Number of petals*.—5.
*Sepal*.—Tubular in configuration.
*Length of calyx*.—Approximately 1.0 cm.
*Anthocyanin pigmentation of calyx limb*.—Present.
*Shape of pistil*.—Two lobes.
*Color of anther*.—Yellowish green.
*Diameter of peduncle*.—Medium.
*Length of peduncle*.—Medium.
*Number of flowers*.—Many.
*Flower bearing*.—In a cluster.

*Reproductive organs.*—1 pistil and 4 stamens.
*Pollen.*—Brilliant greenish-yellow (near R.H.S. 6C) in coloration.
*Flower fragrance.*—Absent.
*Flowering time.*—Early.
*Flowering duration.*—Long. When planted during March, the plant commonly blooms from April to November. A bloom cluster commonly is present for approximately 2 to 3 weeks, and an individual bloom within the cluster commonly lasts for approximately 7 to 10 days on the plant. The plant is highly tolerant to heat, and exhibits a high resistance to diseases, particularly powdery mildew, and a high resistance to pests.

SUMMARY OF THE NEW VARIETY

The new variety of *Verbena* plant has a broad spreading growth habit and long stems. The plant is well branched and abundantly forms flowers in a cluster. The blooms are present in profusion. The blooming period is April to November and flowering duration is long. The entire plant remains in bloom for an extended period of time. The flower size is large and the petal coloration of the flowers is light purplish pink. The plant is highly tolerant to heat, exhibits a high resistance to pests and diseases, particularly powdery mildew. The plant has very low self-fertility.

DESCRIPTION OF THE VARIETY

Figure 1:
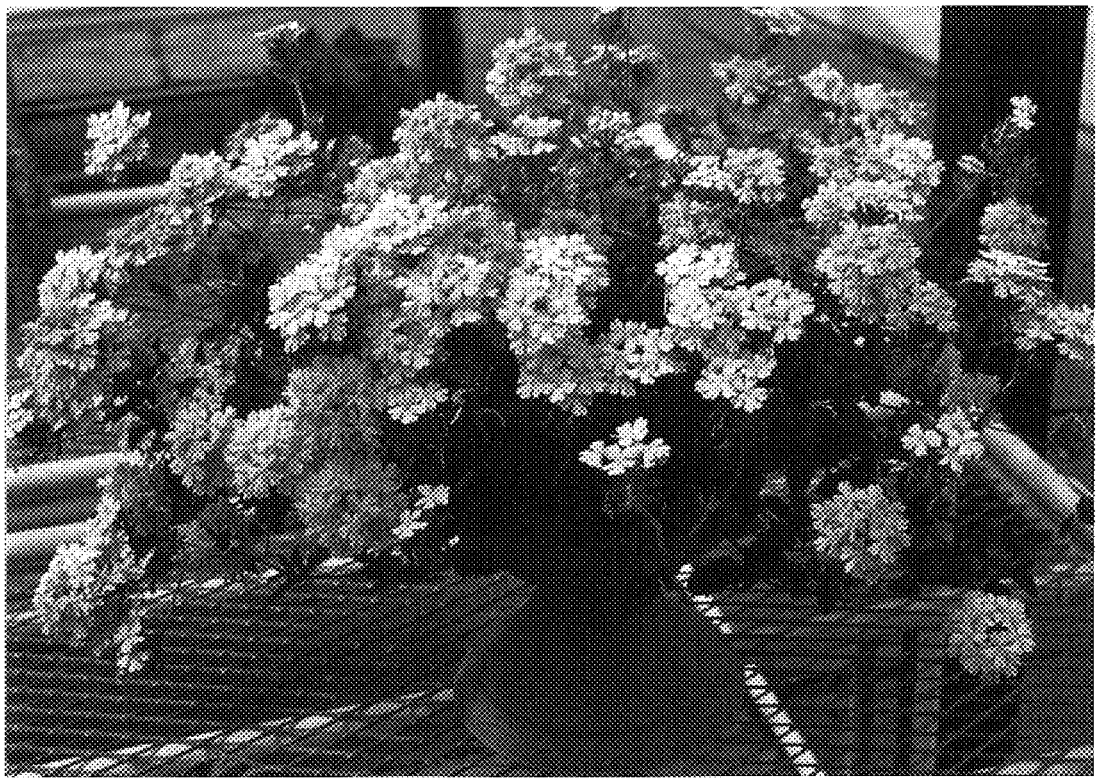
FIG. 1 depicts a side view of the 'Sunmarisakura' plant of the present invention.
Figure 2:
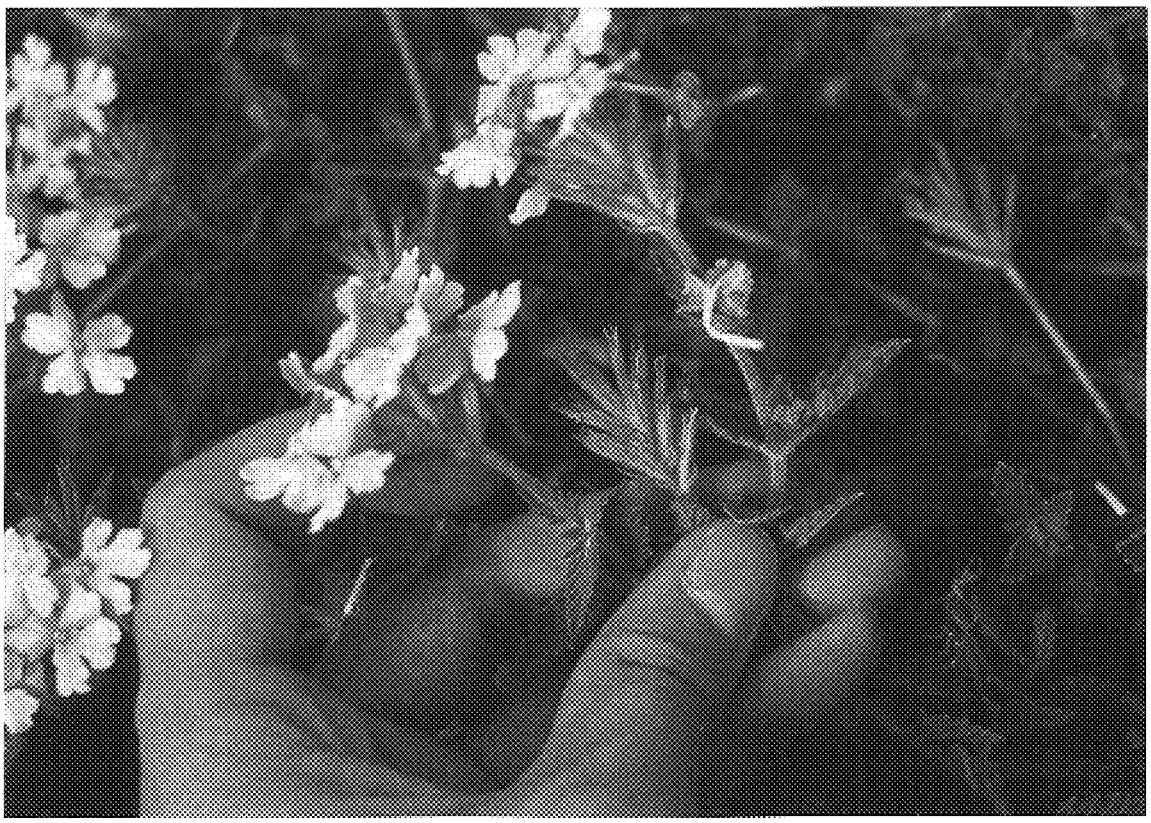
FIG. 2 depicts a close-up view of the flowers of the 'Sunmarisakura' plant of the present invention.

The botanical characteristics of the new and distinct variety of *Verbena* plant, 'Sunmarisakura' are as follows when grown at Yokaichi-shi, Shiga-ken, Japan.

Plant:
*Growth habit.*—Decumbent.
*Plant width.*—Approximately 65–71 cm.
*Plant height.*—Approximately 8–9 cm.
Stem:
*Diameter.*—Approximately 1.7–2.2 mm.
*Anthocyanin pigmentation.*—Absent.
*Pubescence.*—Normal.
*Branching.*—A moderate level of branching is present.
*Subterranean stem.*—Absent but when the stems contact the surface of soil, the nodes take root in the ground and the plant growth thereby spreads.
*Length of internode.*—Approximately 1.7–2.7 cm.
Leaf:
*Phyllotaxis.*—Opposite.
*Shape.*—Oblong-lanceolate.
*Depth of incision.*—Shallow.
*Margin.*—Serrate.
*Length.*—Approximately 2.9–3.6 cm.
*Width.*—Approximately 1.6–2.4 cm.
*Leaf apex.*—Mucronate.
*Leaf base.*—Petiolate.
*Color.*—Dark olive green (near R.H.S. 141A) on the upper surface. Near R.H.S. 138A on the lower surface.
*Pubescence.*—Sparse.
*Petiole.*—Present.
*Thickness of petiole.*—Approximately 1.0–1.2 mm.
*Length of petiole.*—Approximately 1.2–2.5 mm.
Flower: Self-cleaning.
*Shape of cluster.*—Obovate.
*Length of cluster.*—Approximately 2.3–4.4 cm.
*Diameter of cluster.*—Approximately 4.0–5.8 cm.
*Facing direction.*—Upward.
*Outward curvature of petal.*—Flat.
*Diameter.*—Approximately 1.8–1.9 cm.
*Height.*—Approximately 2.1–2.2 cm.
*Color.*—Light purplish pink (near R.H.S. 62C) on the upper surface. Near R.H.S. 65A on the lower surface.
*Eye color.*—Pale yellow (near R.H.S. 11D).
*Eye size.*—Small.
*Variegation on petal.*—Absent.
*Color presentation.*—Substantially even.
*Color intensity.*—Absent.
*Incision of petal.*—Present.
*Number of petals.*—5.
*Sepal.*—Tubular in configuration.
*Length of calyx.*—Approximately 1.2–1.4 cm.
*Anthocyanin pigmentation of calyx limb.*—Absent.
*Shape of pistil.*—Two lobes.
*Color of anther.*—Yellowish green (near R.H.S. N144D).
*Peduncle length.*—Approximately 2.1 cm.
*Peduncle diameter.*—Approximately 1.5 mm.
*Flower bearing.*—In a cluster.
*Reproductive organs.*—1 pistil and 4 stamens.
*Pollen.*—Scarce. Brilliant greenish-yellow (Near R.H.S. 6C) in coloration.
*Stigma color.*—Near R.H.S. 144A.
*Style color.*—Near R.H.S. 144C.
*Ovary color.*—Near R.H.S. 144B.
*Flower fragrance.*—Absent.
*Flowering time.*—Early.
*Flowering duration.*—Long. When planted during March, the plant commonly blooms from April to November. A bloom cluster commonly is present for approximately 2 to 3 weeks, and an individual bloom within the cluster commonly lasts for approximately 7 to 10 days on the plant. The plant is highly tolerant to heat. The plant grows well at temperatures up to at least 35° C., and exhibits a high resistance to diseases, particularly powdery mildew. No serious damage by pathogens and pests common to *Verbena* has been observed.

This new variety of *Verbena* plant is most suitable for flower bedding and potting, particularly in planters, and is further excellent for use in a hanging basket.

The plant of this new variety, 'Sunmarisakura', is presently planted and maintained at Yokaichi-shi, Shiga-ken, Japan.

It is claimed:

1. A new and distinct variety of *Verbena* hybrida plant named 'Sunmarisakura', substantially as herein illustrated and described.

* * * * *